United States Patent [19]
Wade

[11] Patent Number: 4,734,413
[45] Date of Patent: Mar. 29, 1988

[54] SUBSTITUTED 1,2,4-TRIAZOLO[1,5-A]TRIAZINES AS BRONCHODILATORS

[75] Inventor: James J. Wade, St. Paul, Minn.
[73] Assignee: Riker Laboratories, Inc., St. Paul, Minn.
[21] Appl. No.: 20,861
[22] Filed: Mar. 2, 1987
[51] Int. Cl.$^4$ ............... A61K 31/54; A61K 31/535; C07D 487/04; C07D 405/04
[52] U.S. Cl. .................. 514/222; 514/227; 514/246; 544/212; 544/206; 544/113; 544/61
[58] Field of Search ............ 514/222, 227, 246; 544/212, 206, 113, 61

[56] References Cited

U.S. PATENT DOCUMENTS 4,572,910  2/1986  Wade .................. 514/222

FOREIGN PATENT DOCUMENTS 122978  10/1984  European Pat. Off. .
205905  1/1984  German Democratic Rep. .

OTHER PUBLICATIONS

Gilardi, Chemical Abstracts, vol. 79, entry 140503x (1973).
E. Taylor & R. Hendess, J. Am. Chem. Soc., 87, 1980 (1965).
R. Bokladere & V. Grinshtein, Chem. of Heter. Compounds, 6, 522–523 (1970).
R. Bokladere & A. Liepin, Chem. of Heter. Compounds, 9, 256–260 (1973).
R. Bokladere et al., Chem. of Heter. Compounds, 9, 388–391 (1973).
L. Capuano & H. Schrepfer, Chem. Ber., 104, 3039–3047 (1971).
T. Hirata et al., J. Heterocycl. Chem., 9, 99 (1972).
S. Langdon et al., J. Chem. Soc., 993–998 (1984).
J. Svetlik, Heterocycles, 20, 1495–9 (1983).
J. Kobe et al., Monatsh. Chem., 97, 1713–1722 (1966).
R. Deshpande and A. Rama Rao, Synthesis, 863–865 (1974).

*Primary Examiner*—John M. Ford
*Attorney, Agent, or Firm*—Donald M. Sell; James A. Smith; Robert W. Sprague

[57] ABSTRACT

Substituted 1,2,4-triazolo[1,5-a]triazines as bronchodilators are disclosed. Pharmaceutical formulations comprising such compounds and pharmacological methods of using such compounds are also described.

7 Claims, No Drawings

SUBSTITUTED 1,2,4-TRIAZOLO[1,5-A]TRIAZINES AS BRONCHODILATORS

TECHNICAL FIELD

The present invention relates to triazolo[1,5-a]triazines, and more specifically to 1,2,4-triazolo[1,5-a]triazines. The pharmacological use of the compounds of the invention as bronchodilators, and pharmaceutical compositions comprising the compounds are also within the scope of the invention.

BACKGROUND OF THE INVENTION

Some 1,2,4-triazolo[1,5-a]triazines are known to the art. Certain 1,2,4-triazolo[1,5-a]triazines are disclosed as being pharmaceuticals, and some are said to be bronchodilators. In the patents discussed below, some of the compounds which are triazolo[1,5-a]triazines are referred to therein as triazolo[2,3-a]triazines.

East German Patent No. 205,905 discloses substituted 1,2,4-triazolo[2,3-a]triazines which are prepared by reacting a 5-amino-1,2,4-triazole-1-thiocarboxamide with an orthoester to provide compounds which are substituted at ring position 2 by thioalkyl or (un)substituted thiobenzyl; position 5 by thio; position 6 by alkyl, (un)-substituted benzyl or aryl; and position 7 by (un)substituted alkyl.

European Patent Appln. No. 122,978 discloses 1,2,4-triazolo[1,5-a]triazines optionally substituted in the 2-position by hydrogen or methyl; in the 5-position by hydroxy or amino; and in the 7-position by hydrogen, thio, hydroxy, alkythio or amino. These compounds are claimed to have gastric acid secretion reducing activity.

The following related articles disclose the syntheses of certain 1,2,4-triazolo[1,5-a]triazines.

E. Taylor and R. Hendess, J. Am. Chem. Soc., 87 1980 (1965), disclose triazolo[2,3-a]triazines, the unsubstituted parent system with oxygen at position 5(5-azahypozanthine) or amino at position 5. These were synthesized as potential purine antagonists.

R. Bokladere and V. Grinshtein, Chemistry of Heterocyclic Compounds (originally published in Khimiya Geterotsiklicheskikh Soidinenii), 6, 522–523 (1970), report the syntheses of various 5-amino-1,2,4-triazolo[1,5-a]triazines by cyclization of 3-amino-2-guanyltriazoles with triethyl orthoformate or formic acid. These compounds were substituted by alkyl or phenyl in the 2-position and optionally by amino in the 7-position. R. Bokladere and A. Liepin, Chemistry of Heterocyclic Compounds, 9, 256–260 (1973), report their study of the reaction of 3-aminotriazoles with carbethoxyisothiocyanate, and subsequent cyclizations to give 1,2,4-triazolo[1,5-a]triazines substituted in the 5 and 7-positions by oxygen or sulfur. R. Bokladere et al., Chemistry of Heterocyclic Compounds, 9, 388–391 (1973), describe the preparation of 7-methylthio-triazolo[1,5-a]triazines by alkylation of triazolylthioureas with iodomethane, and subsequent cyclization with triethyl orthoformate.

L. Capuano and H. Schrepfer, Chem. Ber., 104, 3039–3047 (1971), disclose 1,2,4-triazolo[1,5-a]triazines substituted by oxo in the 5-position; thio in the 7-position; and hydrogen or methyl in the 8-position.

T. Hirata et al., J. Heterocycl. Chem., 9, 99 (1972), describe some reactions of 3-amino-1,2,4-triazole with isocyanates and isothiocyanates, and subsequent cyclizations to 1,2,4-triazolo[1,5-a]triazines having an oxo or a thio substituent in the 5-position.

S. Langdon et al., J. Chem. Soc., 993–998 (1984), disclose 1,2,4-triazolo[1,5-a]triazines substituted by (un)substituted phenyl in the 2-position; and either dimethylamino in both 5- and 7-positions or morpholino in both the 5- and 7-positions.

J. Svetlik, Heterocycles, 20, 1495–9 (1983), discloses 1,2,4-triazolo[1',5':1,2]-1,3,5-triazino[5,6-a]-benzimidazole, but not the triazolo[1,5-a]triazines as such.

J. Kobe et al., Monatsh. Chem., 97, 713–22 (1966), disclose the synthesis of substituted triazolo[4,3-a]triazines. Subsequently, J. Kobe et al., Tetrahedron, 26, 3357–3368 (1970), disclose 1,2,4-triazolo[2,3-a]triazines as isomeric products formed on rearrangement of the corresponding products of the [4,3-a]series.

R. Deshpande and A. Rama Rao, Synthesis, 863–865 (1974), disclose the synthesis of 3-alkyl and 3-aryl triazolo[4,3-a]triazines from acyl derivatives of symmetrically substituted 2-hydrazino-3-triazines. These compounds, which contained a substituted amino moiety such as morpholino in the 5- and 7-positions, were subsequently isomerized to the corresponding triazolo[2,3-a]triazines.

Bronchodilator triazolo[1,5-c]pyrimizines substituted by a cyclic amino moiety are known. For example, U.S. Pat. No. 4,572,910 discloses substituted triazolo[1,5-c]pyrimidines which differ from triazolo[1,5-a]triazines in that N replaces C at ring position 8. These compounds are substituted on the pyrimidine ring in position 5 and/or 7 by a cyclic amino group such as piperidino, piperazino, morpholino or thiomorpholino bonded through the nitrogen atom to the pyrimidine ring. These compounds may also contain alkyl in the 5-position.

DETAILED DESCRIPTION OF THE INVENTION

The present invention relates to 1,2,4-triazolo[1,5-a]triazines which are bronchodilators. The invention also relates to the method for inducing bronchodilation in the mammal using a 1,2,4-triazolo[1,5-a]triazine of the invention, and to bronchodilator pharmaceutical compositions comprising an effective amount of a 1,2,4-triazolo[1,5-a]triazine of the invention, together with a pharmaceutically acceptable carrier.

Specifically, the present invention relates to bronchodilator compounds of Formula I

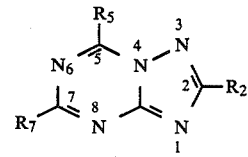

wherein $R_2$ is hydrogen, lower alkyl, or phenyl; $R_5$ is lower alkyl; and $R_7$ is methoxy, methylthio or

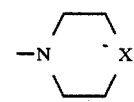

wherein X is independently oxygen, sulfur, methylene (—CH2—), imido (—NH—) or

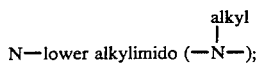

and pharmaceutically acceptable acid-addition salts therein.

"Lower alkyl", as used in the instant specification and claims, designates straight or branched-chain alkyl groups containing one to about four carbon atoms. Preferred lower alkyl substituents are methyl and ethyl.

The presently preferred compounds of the invention have generally higher potency in protecting against histamine-induced contractions of isolated guinea pig tracheal tissue. This assay is discussed in greater detail below. Specific examples of preferred compounds which are active in the aforementioned assay at concentrations of 5 ug per ml or lower are:

5-ethyl-7-(4-thiomorpholino)-1,2,4-triazolo[1,5-a]triazine,
5-ethyl-7-(4-morpholino)-1,2,4-triazolo[1,5-a]triazine,
5-methyl-7-methylthio-1,2,4-triazolo[1,5-a]triazine,
5-methyl-7-[1-(4-methylpiperazino)]-1,2,4-triazolo[1,5-a]triazine,
5-ethyl-2-methyl-7-methylthio-1,2,4-triazolo[1,5-a]triazine,
5-ethyl-2-methyl-7-(4-morpholino)-1,2,4-triazolo[1,5-a]triazine,
5-ethyl-7-[1-(4-methylpiperazino)]-1,2,4-triazolo[1,5-a]triazine,
5-ethyl-7-methoxy-1,2,4-triazolo[1,5-a]triazine,
2,5-dimethyl-7-(4-thiomorpholino)-1,2,4-triazolo[1,5-a]triazine,
2,5-diethyl-7-(4-morpholino)-1,2,4-triazolo[1,5-a]triazine,
5-ethyl-2-methyl-7-(4-thiomorpholino)-1,2,4-triazolo[1,5-a]triazine,
5-ethyl-2-methyl-7-[1-(4-methylpiperazino)]-1,2,4-triazolo[1,5-a]triazine, and
2,5-diethyl-7-(4-thiomorpholino)-1,2,4-triazolo[1,5-a]triazine.

The presently preferred compounds of Formula I are the last three mentioned above.

The bronchodilator activity of the compounds of Formula I was assessed by the measurement of effects on isolated tracheal spirals. This is a well-known and long established in vitro test method. The bronchodilator activity was determined according to the following procedure: Female guinea pigs were sacrificed and each trachea removed and cut into a spiral strip. This strip was mounted in a constant temperature (37° C.) muscle bath having a volume of approximately 15ml. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, acetylcholine and barium chloride. The amount of a given compound of Formula I (measured in ug/ml) required to provide greater than 75% relaxation of drug-induced contraction is considered an effective concentration. For comparison, a well known standard brochodilator, aminophylline, required concentrations of 50 ug/ml versus histamine, 100 ug/ml versus acetylcholine and 10 ug/ml versus barium chloride to provide greater than 75% relaxation.

The compounds of Formula I which were most active in the in vitro test, including most of those listed above as preferred compounds, were tested in vivo in guinea pigs for bronchodilator activity using the so-called Konzett-Rossler in vivo test method. The bronchodilator activity was determined according to the procedure which follows: The Konzett-Rossler technique [H. Konzett and R. Rossler, Naunyn-Schmiedebergs Arch. Pharmakol., 195, 71–74 (1940)] was used to assess the effect of test drugs on antigen challenge of male Hartley strain guinea pigs (350–500 g). Sensitized (50 mg/kg ovalbumin, i.p., 14–21 days previously) or naive animals were anesthetized with pentobarbital (70 mg/kg, i.p.) and spontaneous respiration was eliminated with succinylcholine (2 mg/kg, i.p.). The trachea was cannulated and respiration maintained under positive pressure with a miniature ventilator (5 ml/breath, 87/minute, 10 cm water). Bronchoconstrictor responses were represented as increased excursions of the tracing on a physiological recorder of air overflow to the lungs measured by a pneumotachograph in series with a differential pressure transducer. Sensitized animals were challenged with ovalbumin (100 ug/kg, i.v.) 30 or 60 minutes, respectively, after the i.p. or p.o. administration of test drugs. Active compounds are those which demonstrate an intraperitoneal or oral $IC_{50}$ of 25 mg per kg or less, and preferably an $IC_{50}$ of 10 mg per kg or less. Most preferred compounds are active at 10 mg per kg.

The compounds of Formula I may be administered to mammals in order to obtain bronchodilation. The compounds may be administered orally, parenterally or by inhalation. Preferably they are administered orally in tablets or capsules. The usual effective human dose will be in the range of 0.1 to 50 mg/kg of body weight.

Pharmaceutically acceptable acid-addition salts of compounds of Formula I are generally prepared by reaction with an equimolar amount of a relatively strong acid, preferably an inorganic acid such as hydrochloric, sulfuric or phosphoric acid, in a polar solvent. Isolation of the salt is facilitated by the addition of a solvent in which the salt is insoluble. An example of such a solvent is diethyl ether.

The compounds of Formula I, either as the free base or in the form of a pharmaceutically acceptable acid-addition salt, can be combined with conventional pharmaceutical dilutents and carriers to form such dosage forms as tablets, capsules, suspensions, solutions, suppositories and the like.

The pharmaceutical carrier employed may be, for example, either a solid or liquid. Examples of solid carriers are lactose, terra alba, sucrose, talc, gelatin, agar, pectin, acacia, magnesium stearate, stearic acid, and the like. Liquid carriers include syrup, peanut oil, olive oil, water and the like. Similarly, the carrier or diluent can include a time delay material well known to the art, such as glyceryl monostearate or glyceryl distearate, these being employed alone or, for example, in combination with a wax.

The compounds may be prepared by the Reaction Scheme shown below, wherein $R_2$ and $R_5$ are as defined above.

Reaction Scheme

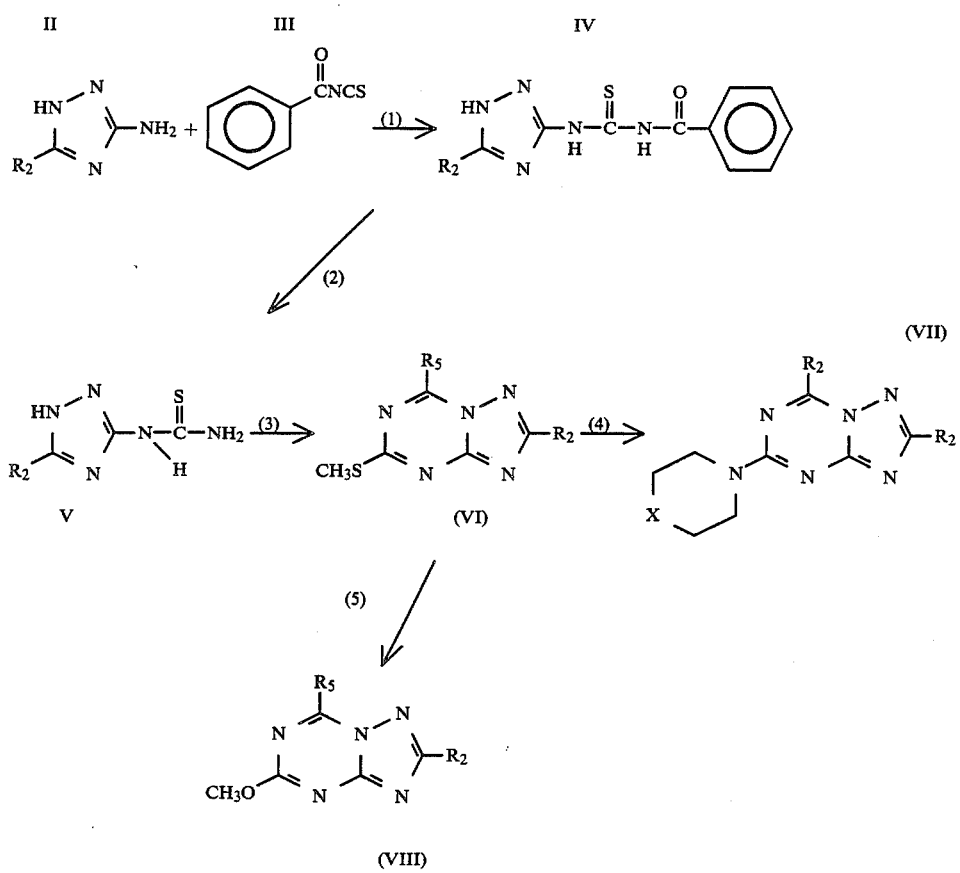

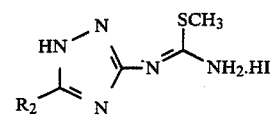

Steps (1) and (2) were carried out by modification of the procedure of G.I. Chipen, R.P. Bokledere and V. Ya Grinshtein, Chemistry of Heterocyclic Compounds, 4, 546–547 (1968), incorporated herein by reference, in which the structure of compounds V were misassigned. The authors later corrected the structures in Chemistry of Heterocyclic Compounds, 9, 256–260 (1973). Steps (1) and (2) were carried out by reacting the amino triazoles of Formula II with 1.1 equivalents of benzoyl isothiocyanate (III) which is preferably prepared in situ and used immediately to form the N'-benzoylthioureas of Formula IV. Base hydrolysis in step (2) using, for example, sodium hydroxide, provides the thioureas of Formula V.

Starting compounds of Formula II are known. Specifically, the compound 3-amino-1,2,4-triazole is known. The compound 3-amino-5-methyl-1,2,4-triazole was prepared as described in Chem. Absts., 51:13934 g, incorporated herein by reference. The compounds 3-amino-5-ethyl-1,2,4-triazole and 3-amino-5-phenyl-1,2,4-triazole were prepared according to the procedure described in K. R. Huffman and F. C. Schaeffer, J. Org. Chem., 28, 1816 (1963), incorporated herein by reference.

Step (3) is carried out by modification of the procedure of K. Bokladere et al., Chemistry of Heterocyclic Compounds, 9, 388–391 (1973), incorporated herein by reference. This step involves a two part synthetic orocess. First, the thiourea of Formula V is reacted with 1.1 to 1.5 equivalents of methyl iodide in a refluxing solvent, preferably a lower chain alcohol, to form the isothiourea hydrogen iodide intermediate The above intermediate thus formed may be isolated by evaporation of the solvent and purified, but generally is taken immediately and suspended in an orthoester which upon heating effects cyclization to the triazolo[1,5-a]triazines of Formula VI. Orthoesters which may be used are of the formula $R_5C(OR)_3$ wherein $R_5$ is as defined in connection with Formula I, and each R is independently lower alkyl. Such orthoesters are known compounds or may be prepared by known methods. Specific examples of suitable orthoesters include trimethyl orthoformate, triethyl orthoformate, triethyl orthoacetate, triethyl orthopropionate and the like. Since the orthoesters are liquids, it is convenient to mix an excess of orthoester with the intermediates formed by the reaction of the compounds of Formula V with methyl iodide, and to heat the mixture at reflux until the reaction is complete. Good yields of the desired solid compounds of Formula VI, which are novel triazolo[1,5-a]triazines of Formula I wherein $R_7$ is alkylthio, are obtained by conventional purification methods.

Step (4) involves reaction of the triazolo[1,5-a]triazines of Formula VI with an amine to form the novel compounds of Formula VII, which is a subgenus of Formula I, wherein R₇ is

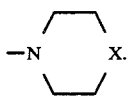

This reaction is carried out in the presence or absence (preferably) of an inert solvent using a secondary organic amine, for example morpholine, thiomorpholine, piperidine, piperazine, or N-methylpiperazine.

Step (5) involves the reaction of methanolic sodium methoxide with a compound of Pormula VI to provide a compound of Formula VIII which is a subgenus of Formula I wherein R₇ is methoxy.

All compounds of Formula I are solids which may be readily isolated by conventional methods such as filtration, extraction or chromatography. Structural assignments may be confirmed by infrared and nuclear magnetic resonance spectral analyses.

The following examples are provided to illustrate the methods used in the invention. They are not intended to limit the invention.

EXAMPLE 1

Preparation of 3-Amino-5-Methyl-1,2,4-Triazole

Following the procedure described in Chem. Absts., 51:13934 g, 132.0 g (2.2 mole) of glacial acetic acid was added to a suspension of 272.2g (2.0 mole) of aminoguanidine bicarbonate in 600 ml of toluene, and the resultant mixture was refluxed, under nitrogen atmosphere, for approximately 4 hours after which time the aminoguanidine bicarbonate had dissolved. Four grams of the catalyst N,N-dimethylaniline was added, and the solution refluxed under a Dean Stark trap until the collection of water ceased. Upon cooling, the crude product which precipitated as a lumpy solid was filtered and dried in a vacuum oven at about 70° C. yielding 188.2 g (96%) of 3-amino-5-methyl-1,2,4-triazole, m.p. 101°-134° C. The product was used crude for further synthesis.

EXAMPLE 2

Preparation of Ethyl N-Cyanoimidate

Using the method of Huffman and Schaeffer, J. Org. Chem., 28, 1816 (1963), 60.0 g (0.341 mole) of triethyl orthopropionate, 14.3 g (0.340 mole) of cyanamide and 69.8 g (0.684 mole) of acetic anhydride were combined and heated to 120° C. at which temperature boiling commenced. The oil bath was removed for a few minutes until vigorous boiling stopped, and the heating was thereafter continued while gradually increasing the bath temperature to about 150° C. and removing the ethyl acetate as a distillate. A vacuum pump was attached and distillation continued, gradually reducing the pressure to approximately 3 mm Hg. After a brief forerun, 36.1g. (84%) of distillate was collected as a clear, colorless liquid of ethyl N-cyanoimidate, b.p. 79°-88° C./3.1-3.4 mm Hg. The structural assignment was confirmed by nuclear magnetic resonance spectral analysis.

EXAMPLE 3

Preparation of 3-Amino-5-ethyl-1,2,4-triazole

To a cooled solution (0°-5° C.) of 89.4g (0.71 mole) of ethyl N-cyanoimidate (from Example 2), in approximately 400 ml of methanol, was added dropwise, with stirring under nitrogen atmosphere, 23.6 g (0.736 mole) of anhydrous hydrazine. When addition was complete (about 15 minutes), the mixture was stirred for approximately 20 minutes in an ice bath, during which time the solution began to turn pink. The solution was then stirred approximately 30 minutes at about 20° C. Concentration in vacuo provided a white solid which was immediately recrystallized from about 1.1 liters of acetonitrile, followed by filtering, washing with ethyl acetate to remove any residual pink color and drying in a vacuum oven to give 51.95 g (65%) of pink needles of 3-amino-5-ethyl-1,2,4-triazole, m.p. 150°-152° C. [lit. (J. Chem. Soc., 1929, 815) m.p. 152° C.]. The structural assignment was confirmed by infrared and nuclear magnetic resonance spectral analyses.

EXAMPLE 4

Preparation of Phenyl N-Cyanoimidate

Using the procedure of Example 2, 50 g (0.274 mole) of trimethyl orthobenzoate, 11.5 g (0.274 mole) of cyanamide and 56.0 g. (0.548 mole) of acetic anhydride were combined and refluxed, followed by vacuum distillation which provided 3 fractions. The third fraction yielded 23.4 g of phenyl N-cyanoimidate, b.p. 117°-123° C. at 4.5 mm Hg. Nuclear magnetic resonance spectral analysis confirmed the structural assignment.

EXAMPLE 5

Preparation of 3-Amino-5-phenyl-1,2,4-triazole

To a solution of 18.85 g (0.118 mole) of phenyl N-cyanoimidate (from Example 4) in approximately 30 ml of methanol was added dropwise with stirring 3.8 g (0.119 mole) of 98% hydrazine. When addition was complete, the solution was allowed to warm to about 20° C. The solution was then cooled and crystals which precipitated were isolated by suction filtration. The filtrate was concentrated in vacuo, and the residue was recrystallized from water and collected. Both crops, which were dried in a vacuum oven and confirmed by nuclear magnetic resonance spectroscopy to be the desired product, were combined to provide 14.8 g (79%) of 3-amino-5-phenyl-1,2,4-triazole.

STEP 1 OF REACTION SCHEME—PREPARATION OF N-(1,2,4-TRIAZOLO-5-YL)-N'-BENZOYLTHIOUREAS

EXAMPLE 6

Preparation of N-(1,2,4-Triazolo-5-yl)-N'-Benzoylthiourea

To a stirred solution of 6.23g (81.9 mmole) of ammonium thiocyanate in about 25 ml of acetone at approximately 50° C. was added, within about 2 minutes, 11.23 g (79.9 mmole) of benzoyl chloride, precipitating immediately a white solid. The mixture was stirred an additional 10 minutes at 50° C., and the solid was then removed by suction filtration and washed with acetone until white. The acetone filtrate was added to a mixture of 3-amino-1,2,4-triazole in approximately 20 ml of dry dimethylformamide, and the mixture was refluxed under a nitrogen atmosphere for about 2 hours, and thereafter concentrated in vacuo. The residue was poured slowly into approximately 450 ml of stirred water at about 20° C., and the oily yellow precipitate which formed solidified with continued stirring. The solution was heated to boiling at which time the minimum amount of ethanol was added to effect complete dissolution. The mixture was then allowed to cool to about 20° C., resulting in the precipitation of a solid which was further cooled in ice and filtered. The solid obtained was slurried in approximately 200 ml of water, and was then filtered and dried in a vacuum oven at about 100° C. to yield 8.2 g (42%) of N-(1,2,4-triazolo-5-yl)-N'-benzoylthiourea as an off-white solid. Nuclear magnetic resonance spectroscopy confirmed the structural assignment.

EXAMPLE 7

Preparation of N-(3-Methyl-1,2,4-triazolo-5-yl)-N'-Benzoylthiourea

A mixture of 7.9 g (80.5 mmole) of 3-amino-5-methyl-1,2,4-triazole (from Example 1) and 14.0 g (85.8 mmole) of benzoyl isothiocyanate were combined in approximately 100 ml of acetone and refluxed for about 20 hours. The mixture was then cooled in an ice bath, filtered and washed with acetone. The solid was slurried in about 100 ml of water, filtered, and then washed sequentially with water and a small amount of ethanol. Drying in a vacuum oven at approximately 100° C. provided 11.3 g (53%) of N-(3-methyl-1,2,4-triazolo-5-yl)-N'-benzoylthiourea. The structural assignment was confirmed by both infrared and nuclear magnetic resonanc spectral analyses.

EXAMPLE 8

Preparation of N-(3-Ethyl-1,2,4-triazolo-5-yl)-N'-Benzoylthiourea

Using the method of Example 6, the benzoyl isothiocyanate was prepared. The yellow-orange filtrate was added to a suspension of 3-amino-5-ethyl-1,2,4-triazole (from Example 3) in acetone and the mixture was refluxed for approximately 3 hours. The mixture was then cooled, filtered, washed with acetone and dried to give N-(3-ethyl-1,2,4-triazolo-5-yl)-N'-benzoylthiourea in 48.5% yield. The structural assignment was confirmed by nuclear magnetic resonance spectral analysis.

EXAMPLE 9

Preparation of N-(3-Phenyl-1,2,4-triazolo-5-yl)-N'-Benzoylthiourea

Using the procedure of Example 8, N-(3-phenyl-1,2,4-triazolo-5-yl)-N'-benzoylthiourea was provided in 43% yield. The structural assignment was confirmed by infrared spectral analysis.

STEP 2 OF REACTION SCHEME—PREPARATION OF N-(1,2,4-TRIAZOL-5-YL)THIOUREAS

EXAMPLE 10

Preparation of N-(1,2,4-Triazol-5-yl)thiourea

N-(1,2,4-triazol-5-yl)-N'-benzoylthiourea (26.0 g, 0.105 mole), from Example 6, was added at once to approximately 100ml of a 10% sodium hydroxide solution which had been preheated to boiling, and the resultant mixture was refluxed for 45 minutes. The solution was then cooled and acidified to approximately pH 3 with the addition of concentrated hydrochloric acid to provide a white solid precipitate. The solid was filtered, washed with water and dried for about 16 hours in a vacuum oven at approximately 100° C. The resultant off-white solid was stirred with about 150 ml of diethyl ether and filtered, and this procedure was repeated. The solid thus obtained was dried in a vacuum oven at about 50° C. to yield 10.4 g (69%) of N-(1,2,4-triazol-5-yl)thiourea as an off-white solid. The structural assignment was confirmed by nuclear magnetic resonance spectral analysis.

EXAMPLES 11–13

Using the procedure of Example 10, the intermediate N'-benzoylthioureas prepared in Examples 7–9 were hydrolyzed to provide thioureas of Formula V (Table I below).

TABLE I

| Example | Thioureas of Formula V $R_2$ |
|---|---|
| 11 | —CH$_3$ |
| 12 | —CH$_2$CH$_3$ |
| 13 | —C$_6$H$_5$ (phenyl) |

STEP 3 OF REACTION SCHEME—PREPARATION OF 7-METHYLTHIO-1,2,4-TRIAZOLO[1,5-a]TRIAZINES

EXAMPLE 14

Preparation of 5-Ethyl-7-methythio-1,2,4-triazolo[1,5-a]triazine

To a suspension of 4.0 g (28.0 mmole) of N-(1,2,4-triazol-5-yl)thiourea (from Example 10), in approximately 50 ml of ethanol was added 4.55 g (32.1 mmole) of methyl iodide and the resultant mixture was refluxed for about 1 hour. The mixture was then concentrated in vacuo, and the residue was suspended in about 20 ml of triethyl orthopropionate and heated at approximately 100° C. for about 2.5 hours. At this point thin layer chromatographic analysis, eluting with dichloromethane, indicated complete conversion to the desired product. The solvent was removed by evaporation and the resultant bright yellow solid was flash chromatographed, eluting with 1:20 ethyl acetate: dichloromethane. Fractions 5–15, which showed no evidence of impurity via thin layer chromatographic analysis, were combined and concentrated in vacuo to provide approximately 3.5 g of a bright yellow solid. The solid was then recrystallized (charcoaled) from benzene:hexanes (2:5 by volume), and was then filtered, washed with hexanes and dried to yield 2.63 g (39%) of a pale yellow solid, 5-ethyl-7-methylthio-1,2,4-triazolo[1,5-a]triazine, m.p. 90°–91° C. Analysis: Calculated for C$_7$H$_9$N$_5$S: % C, 43.06; % H, 4.65; % N, 35.87; Found: % C, 43.5; % H, 4.7; % N, 36.0. The structural assignment was confirmed by infrared and nuclear magnetic resonance spectral analyses.

EXAMPLES 15–21

Using the method of Example 14, the indicated intermediates of Formula V were reacted with the specified orthoesters to provide the indicated compounds of Formula VI (Table II).

TABLE II

| EXAMPLE | Intermediate of Formula V R₂ | Orthoester | Intermediate of Formula VI R₂ | R₅ | Calculated: % C, % H, % N<br>Found: % C, % H, % N<br>(m.p. in °C.) |
|---|---|---|---|---|---|
| 15 | H | triethyl orthoacetate | H | CH₃ | 39.8; 3.9; 38.7<br>39.8; 3.9; 39.2<br>(116-119) |
| 16 | CH₃ | triethyl orthoacetate | CH₃ | CH₃ | 43.06; 4.65; 35.87<br>42.6; 4.6; 35.9<br>(111-111.5) |
| 17 | CH₃ | triethyl orthopropionate | CH₃ | CH₂CH₃ | 45.9; 5.3; 33.5<br>46.2; 5.2; 33.8<br>(101-103) |
| 18 | CH₂CH₃ | triethyl orthopropionate | CH₂CH₃ | CH₂CH₃ | (not analyzed) |
| 19 | CH₂CH₃ | triethyl orthoacetate | CH₂CH₃ | CH₃ | (not analyzed) |
| 20 |  | triethyl orthopropionate |  | CH₂CH₃ | (not analyzed) |
| 21 |  | triethyl orthoacetate |  | CH₃ | (not analyzed) |

STEP 4 OF REACTION SCHEME—PREPARATION OF 7-SUBSTITUTED -1,2,4-TRIAZOLO[1,5-a]TRIAZINES

EXAMPLE 22

Preparation of 5-Ethyl-7-(4-thiomorpholino)-1,2,4triazolo[1,5-a]triazine

To 1.5 g (7.69 mmole) of 5-ethyl-7-methylthio-1,2,4triazolo[1,5-a]triazine (from Example 14) was added 0.87 g (8.45 mmole) of thiomorpholine, and the resultant mixture was refluxed for about 20 hours at which time no starting material was evident by thin layer chromatographic analysis, eluting with 1:20 ethyl acetate: dichloromethane. The resultant oil which solidified on cooling was dissolved in chloroform, washed numerous times with water, dried over magnesium sulfate and concentrated in vacuo to provide a yellow solid which was triturated with diethyl ether and filtered to yield 1.21 g (63%) of a pale yellow solid. The solid was recrystallized (charcoaled) from benzene:hexanes (1:2 by volume) to provide, after drying in a vacuum oven at about 50° C., 0.87 g (45%) of 5-ethyl-7-(4-thiomorpholino)-1,2,4-triazolo-[1,5-a]tr 138°-139° C. Analysis: Calculated for $C_{10}H_{14}N_6S$: % C, 48.0; % H, 5.6; % N, 33.6; Found: % C, 48.4; % H, 5.6; % N, 33.4. The structure was confirmed by infrared and nuclear magnetic resonance spectral analysis.

EXAMPLES 23-42

Using the method of Example 22, the indicated intermediates of Formula VI were reacted with the designated amine to provide the novel compounds of Formula VII (Table III below). The structures were confirmed by infrared and nuclear magnetic resonance spectral analyses.

TABLE III

| EXAMPLE | Intermediate of Formula VI R₂ | R₅ | Amine | Product of Formula VII R₂ | R₅ | R₇ | Calculated: % C, % H, % N<br>Found: % C, % H, % N<br>(m.p. in °C.) |
|---|---|---|---|---|---|---|---|
| 23 | CH₃ | CH₃ | 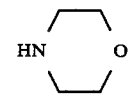 | CH₃ | CH₃ | 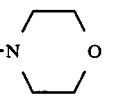 | 51.3; 6.0; 35.9<br>51.4; 5.9; 35.8<br>(152-153) |
| 24 | H | CH₂CH₃ | 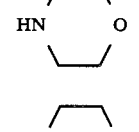 | H | CH₂CH₃ | 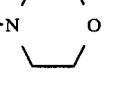 | 51.3; 6.0; 35.9<br>51.7; 6.0; 35.9<br>(163-165) |
| 25 | H | CH₃ | 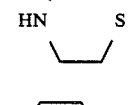 | H | CH₃ | 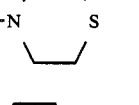 | 45.7; 5.1; 35.6<br>45.7; 5.1; 35.7<br>(164-165.5) |
| 26 | H | CH₃ | 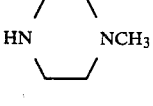 | H | CH₃ | 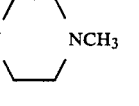 | 51.5; 6.5; 42.0<br>51.6; 6.5; 41.7<br>(123.5-125) |

TABLE III-continued

| EXAMPLE | Intermediate of Formula VI | | Amine | Product of Formula VII | | | Calculated: % C, % H, % N Found: % C, % H, % N (m.p. in °C.) |
|---|---|---|---|---|---|---|---|
| | $R_2$ | $R_5$ | | $R_2$ | $R_5$ | $R_7$ | |
| 27 | $CH_3$ | $CH_2CH_3$ | HN⌬O | $CH_3$ | $CH_2CH_3$ | —N⌬O | 53.2; 6.5; 33.9<br>53.6; 6.5; 34.2<br>(131–132) |
| 28 | H | $CH_2CH_3$ | HN⌬NCH$_3$ | H | $CH_2CH_3$ | —N⌬NCH$_3$ | 53.4; 6.9; 39.6<br>53.1; 6.9; 39.2<br>(103–106) |
| 29 | $CH_3$ | $CH_2CH_3$ | HN⌬S | $CH_3$ | $CH_2CH_3$ | —N⌬S | 50.0; 6.1; 31.8<br>50.2; 6.1; 31.7<br>(129–132) |
| 30 | $CH_3$ | $CH_2CH_3$ | HN⌬NCH$_3$ | $CH_3$ | $CH_2CH_3$ | —N⌬NCH$_3$ | 55.2; 7.3; 37.5<br>55.1; 7.2; 37.1<br>(92–93) |
| 31 | H | $CH_3$ | HN⌬O | H | $CH_3$ | —N⌬O | 49.1; 5.5; 38.2<br>49.0; 5.5; 37.6<br>(137–139) |
| 32 | $CH_3$ | $CH_3$ | HN⌬S | $CH_3$ | $CH_3$ | —N⌬S | 48.0; 5.6; 33.6<br>48.1; 5.6; 33.3<br>(161–164) |
| 33 | $CH_3$ | $CH_3$ | HN⌬NCH$_3$ | $CH_3$ | $CH_3$ | —N⌬NCH$_3$ | 53.4; 6.9; 39.7<br>53.5; 6.9; 39.4<br>(111–113) |
| 34 | $CH_2CH_3$ | $CH_2CH_3$ | HN⌬O | $CH_2CH_3$ | $CH_2CH_3$ | —N⌬O | 54.9; 6.9; 32.0<br>55.0; 7.0; 31.6<br>(80–84) |
| 35 | C$_6$H$_5$ | $CH_2CH_3$ | HN⌬O | C$_6$H$_5$ | $CH_2CH_3$ | —N⌬O | 61.9; 5.8; 27.1<br>61.6; 5.8; 27.0<br>(164–166) |
| 36 | C$_6$H$_5$ | $CH_2CH_3$ | HN⌬S | C$_6$H$_5$ | $CH_2CH_3$ | —N⌬S | 58.9; 5.6; 25.7<br>58.6; 5.6; 25.6<br>(195–196) |
| 37 | $CH_2CH_3$ | $CH_2CH_3$ | HN⌬S | $CH_2CH_3$ | $CH_2CH_3$ | —N⌬S | 51.8; 6.5; 30.2<br>51.7; 6.6; 30.0<br>(113–115) |
| 38 | C$_6$H$_5$ | $CH_3$ | HN⌬ | C$_6$H$_5$ | $CH_3$ | —N⌬ | 65.3; 6.2; 28.5<br>64.3; 6.2; 28.3<br>(186–188) |
| 39 | C$_6$H$_5$ | $CH_3$ | HN⌬O | C$_6$H$_5$ | $CH_3$ | —N⌬O | 60.8; 5.4; 28.4<br>60.3; 5.5; 27.9<br>(187–188) |

TABLE III-continued

| EXAMPLE | Intermediate of Formula VI | | Amine | Product of Formula VII | | | Calculated: % C, % H, % N Found: % C, % H, % N (m.p. in °C.) |
|---|---|---|---|---|---|---|---|
| | R₂ | R₅ | | R₂ | R₅ | R₇ | |
| 40 | phenyl | CH₃ | HN⟨thiomorpholine⟩ | phenyl | CH₃ | —N⟨thiomorpholino⟩ | 57.7; 5.2; 26.9 / 57.4; 5.2; 26.8 (204–205) |
| 41 | CH₂CH₃ | CH₃ | HN⟨morpholine⟩ | CH₂CH₃ | CH₃ | —N⟨morpholino⟩ | 53.2; 6.5; 33.8 / 53.2; 6.5; 33.8 (103–104) |
| 42 | CH₂CH₃ | CH₃ | HN⟨thiomorpholine⟩ | CH₂CH₃ | CH₃ | —N⟨thiomorpholino⟩ | 50.0; 6.1; 31.8 / 50.2; 6.1; 31.9 (92–94) |

EXAMPLE 43

Preparation of 2,5-diethyl-7-morpholino-1,2,4-triazolo[1,5-a]triazine bisulfate

The bisulfate salt of the compound of Example 34 was prepared by dissolving 1.01 g (3.85 mmole) of 2,5-diethyl-7-morpholino-1,2,4-triazolo[1,5-a]triazine in approximately 8.0ml of ethyl alcohol with slight warming. To this solution was added dropwise 0.40g (4.1 mmole) of concentrated sulfuric acid and the resultant solution was diluted to about 50 ml with the addition of diethyl ether. The solution was allowed to stand at about 20° C. for several hours, then cooled to approximately 5° C. and maintained at that temperature for about 16 hours, after which time no precipitate was observed. The solution was then slowly diluted with additional diethyl ether until slight cloudiness of the solution was evident. Upon standing at approximately 20° C., a granular solid slowly precipitated. The solution was cooled to about 5° C. for approximately 16 hours, at which time the solid was removed by suction filtration, washed with diethyl ether, and dried to provide 1.02 g (74%) of a pale yellow solid of 2,5-diethyl-7-morpholino-1,2,4-triazolo[1,5-a]triazine bisulfate, m.p. 174°–176° C. Analysis: Calculated for $C_{12}H_{18}N_6O \cdot H_2SO_4$: % C, 40.0; % H, 5.6; % N, 23.3; Found: % C, 39.9; % H, 5.6; % N, 23.5.

STEP 5 OF REACTION SCHEME—PREPARATION OF 7-SUBSTITUTED 1,2,4-TRIAZOLO[1,5-a]TRIAZINES

EXAMPLE 44

One gram (5.1 mmole) of 5-ethyl-7-methylthio-1,2,4-triazolo[1,5-a]triazine was dissolved in approximately 15ml of methanol to which was added about 2ml of a 25% solution of sodium methoxide in methanol. The resultant solution was refluxed for about 24 hours at which time thin layer chromatographic analysis, eluting with 1:1 ethyl acetate: dichloromethane, indicated complete conversion to the desired product. The solution was evaporated in vacuo and the residue was dissolved in water. The aqueous solution was then neutralized with 5% hydrochloric acid solution and extracted thrice with chloroform. The extracts were combined, washed with water, dried over magnesium sulfate, filtered and evaporated in vacuo to yield, after recrystallization from benzene:hexanes, 0.71g of an off-white solid of 5-ethyl-7-methoxy-1,2,4-triazolo[1,5-a]triazine, m.p. 117°–119° C. Analysis: Calculated for $C_7H_9N_5O$: % C, 46.9; % H, 5.1; % N, 39.1; Found: % C, 46.9; % H, 5.0; % N, 38.7. The structural assignment was confirmed by infrared and nuclear magnetic resonance spectral analyses.

EXAMPLE 45

Using the compound obtained in Example 16, and following the procedure of Example 44, 2,5-dimethyl-7-methoxy-1,2,4-triazolo[1,5-a]triazine, m.p. 103°–105° C., was provided in 93% yield. The structural assignment was confirmed by nuclear magnetic resonance spectral analysis. Analysis: Calculated for $C_7H_9N_5O$: % C, 46.9; % H, 5.1; % N, 39.1; Found: % C, 46.9; % H, 5.0; % N, 38.5.

What is claimed is:

1. A compound of the formula

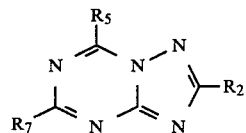

wherein $R_2$ is hydrogen, lower alkyl, or phenyl; $R_5$ is lower alkyl; and $R_7$ is methoxy, methylthio or

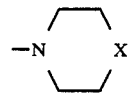

wherein X is independently oxygen, sulfur, methylene, imido or lower N-alkylimido; or a pharmaceutically acceptable acid-addition salt thereof.

2. A compound according to claim 1, wherein X is sulfur or oxygen.

3. A compound according to claim 1, selected from the group consisting of
5-ethyl-7-(4-thiomorpholino)-1,2,4-triazolo[1,5-a]triazine,
5-ethyl-7-(4-morpholino)-1,2,4-triazolo[1,5-a]triazine,
5-methyl-7-methylthio-1,2,4-triazolo[1,5-a]triazine,
5-methyl-7-[1-(4-methylpiperazino)]-1,2,4-triazolo[1,5-a]triazine, 5-ethyl-2-methyl-7-methylthio-1,2,4-triazolo[1,5-a]-triazine,
5-ethyl-2-methyl-7-(4-morpholino)-1,2,4-triazolo[1,5-a]triazine,
5-ethyl-7-[1-(4-methylpiperazino)]-1,2,4-triazolo[1,5-a]triazine,
5-ethyl-2-methyl-7-(4-thiomorpholino)-1,2,4-triazolo[1,5-a]triazine,
5-ethyl-2-methyl-7-[1-(4-methylpiperazino)]-1,2,4-triazolo[1,5-a]triazine,
5-ethyl-7-methoxy-1,2,4-triazolo[1,5-a]triazine,
2,5-dimethyl-7-(4-thiomorpholino)-1,2,4-triazolo[1,5-a]triazine,
2,5-diethyl-7-(4-morpholino)-1,2,4-triazolo[1,5-a]triazine; and
2,5-diethyl-7-(4-thiomorpholino)-1,2,4-triazolo[1,5-a]triazine.

4. A bronchodilator pharmaceutical composition comprising a compound according to claim 1 and a pharmaceutically acceptable vehicle, said compound being present in an amount sufficient to cause bronchodilation.

5. A method for obtaining bronchodilation in a mammal, comprising administering a compound of the formula

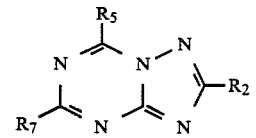

wherein $R_2$ is hydrogen, lower alkyl, or phenyl; $R_5$ is lower alkyl; and $R_7$ is methoxy, methylthio or

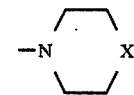

wherein X is independently oxygen, sulfur, methylene, imido or lower N-alkylimido; or a pharmaceutically acceptable acid-addition salt thereof; said compound being administered in an amount sufficient to cause bronchodilation.

6. A method according to claim 5, wherein X is sulfur or oxygen.

7. A method according to claim 5, wherein said compound is administered orally.

* * * * *

UNITED STATES PATENT AND TRADEMARK OFFICE
CERTIFICATE OF CORRECTION

PATENT NO. : 4,734,413

DATED : March 29, 1988

INVENTOR(S) : Wade

It is certified that error appears in the above-identified patent and that said Letters Patent is hereby corrected as shown below:

Col. 2, line 11        Patent:    713-22
                                Should be: 1713-22

Col. 5, line 66 & 67    Patent:    orocess
                                Should be: process Col. 7, line 14        Patent:    Pormula
                                Should be: Formula Col. 12, line 32       Patent:    $[1,5-a]$tr $138°-139°$ C.
                                Should be: $[1,5-a]$triazine, m.p. $138-139°$ C.

Signed and Sealed this

Thirteenth Day of June, 1989

*Attest:*

DONALD J. QUIGG

*Attesting Officer*         *Commissioner of Patents and Trademarks*